United States Patent [19]

Davis

[11] Patent Number: 4,574,850
[45] Date of Patent: Mar. 11, 1986

[54] METHOD OF AND APPARATUS FOR DISPENSING LIQUID

[75] Inventor: James E. Davis, Wilmington, Del.

[73] Assignee: E. I. Du Pont de Nemours and Company, Wilmington, Del.

[21] Appl. No.: 692,409

[22] Filed: Jan. 17, 1985

[51] Int. Cl.[4] .............................................. B65B 3/04
[52] U.S. Cl. ......................................... 141/9; 141/98; 141/90; 73/864.24; 422/100
[58] Field of Search ........... 73/864.01, 864.02, 864.11, 73/864.12, 864.13, 864.14, 864.15, 864.16, 864.17, 864.18, 864.22, 864.23, 864.25; 141/1–12, 18, 67, 89–92; 422/63–67, 100

[56] References Cited

U.S. PATENT DOCUMENTS

| | | | |
|---|---|---|---|
| 3,479,141 | 11/1969 | Smythe et al. | 23/230 |
| 3,484,170 | 12/1969 | Smythe et al. | 356/181 |
| 3,764,041 | 10/1973 | Noll | 222/1 |
| 3,795,149 | 3/1974 | Gillette et al. | 73/423 |
| 3,804,593 | 4/1974 | Smytheb et al. | 23/230 |
| 3,869,068 | 3/1975 | Chen | 222/148 |
| 3,960,020 | 1/1976 | Gordon et al. | 73/423 A |
| 4,121,466 | 10/1978 | Reichler et al. | 73/423 A |
| 4,237,094 | 12/1980 | Suovaniemi et al. | 422/100 |
| 4,259,291 | 3/1981 | Smythe | 422/82 |
| 4,318,885 | 3/1982 | Suzuki et al. | 422/68 |
| 4,367,043 | 1/1983 | Sweet et al. | 356/338 |

Primary Examiner—Houston S. Bell, Jr.

[57] ABSTRACT

A liquid pipetting system for aspirating and dispensing small samples of fluid and diluents. The pipetting system consists of a coaxial needle serving as the pipette tip and a metering system to control the fluids. Precise dispensing of small amounts of liquid from the inner needle is made possible by surrounding the sample liquid with a miscible diluting liquid thereby establishing a controlled interface and conveying the sample liquid into the receiving chamber with that miscible diluting liquid.

12 Claims, 17 Drawing Figures

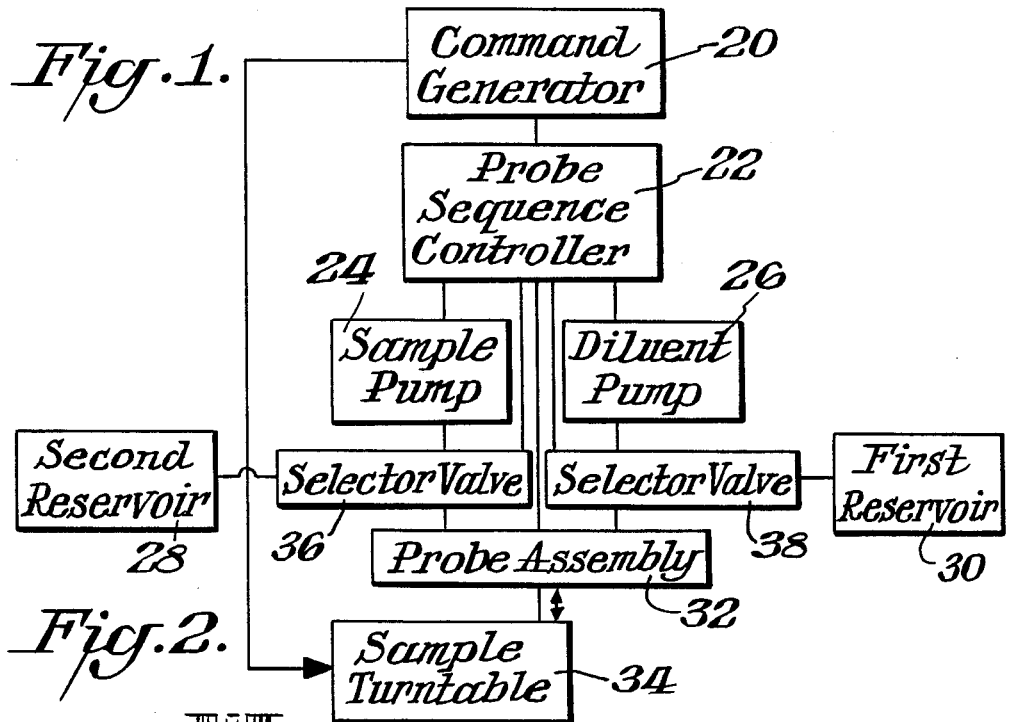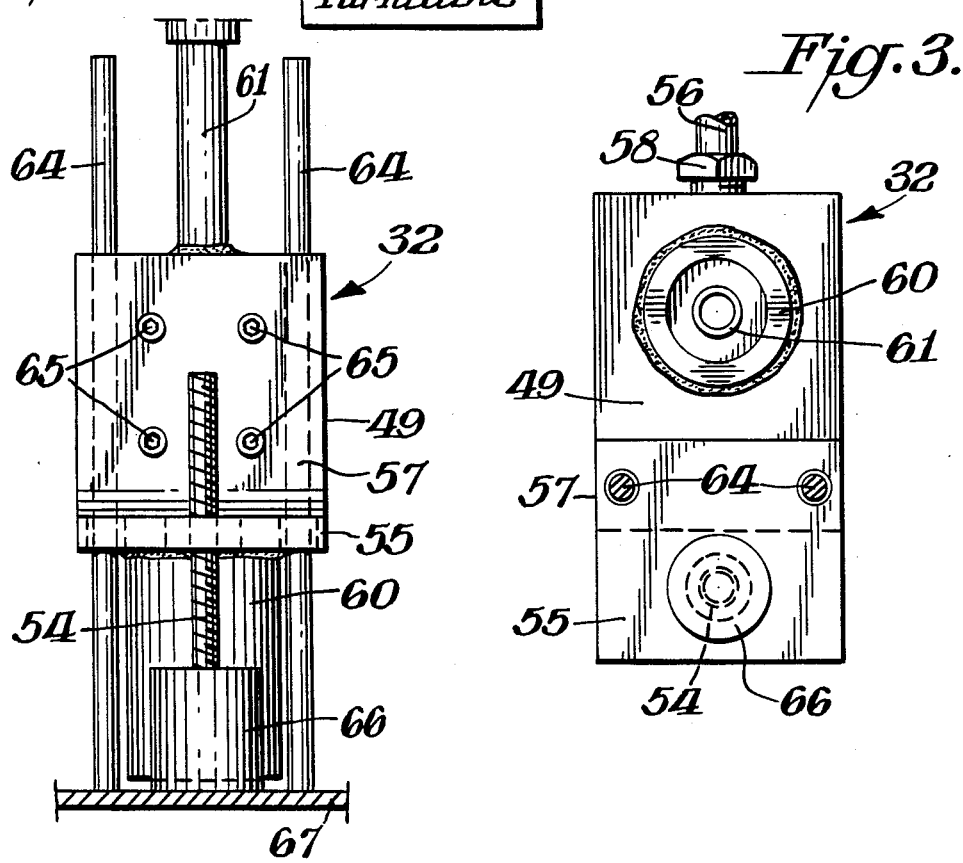

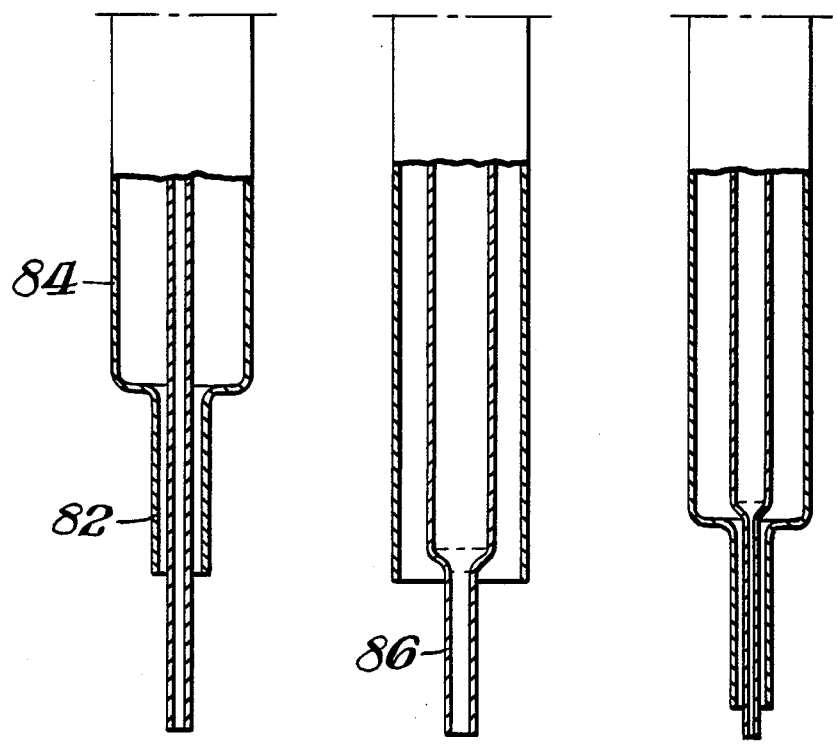

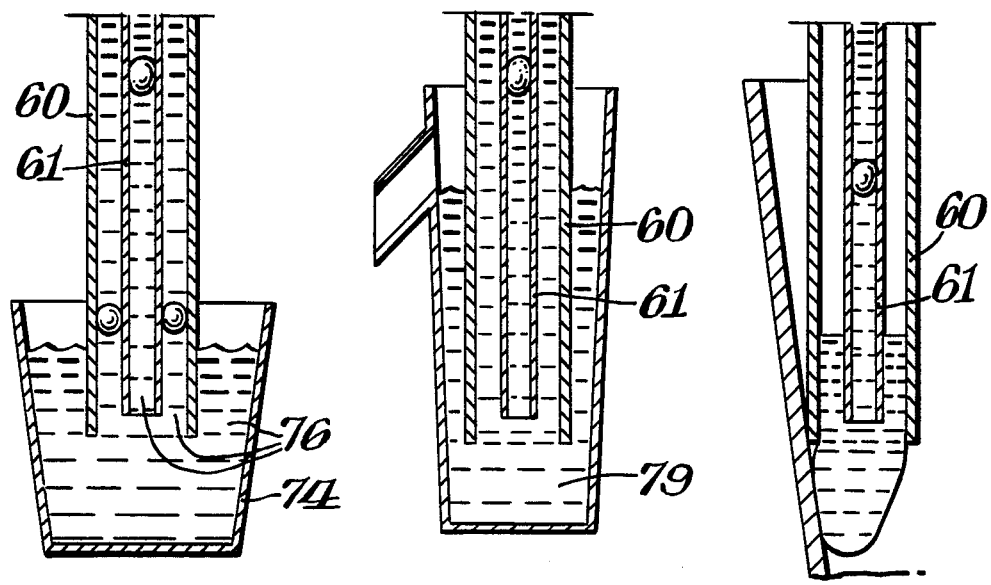

METHOD OF AND APPARATUS FOR DISPENSING LIQUID

BACKGROUND OF THE INVENTION

This invention relates to a method of and apparatus for aspirating and dispensing small volumes of liquid.

With the increasing sophistication of analytical instruments and the ability to precisely measure or detect small quantities of material, the need for accurate dispensing of liquid samples is vitally important. This is particularly relevant when performing clinical analyses where only small quantities of sample are available. Typical sample volumes in the order of several microliters are becoming common in clinical analysis. The problem with small samples arises from the fact that if small quantities of material or sample adhere to either the interior or exterior of the dispensing tube, such quantities can represent a significant portion of the sample to be dispensed. This creates large errors in quantities dispensed. The residual sample also represents a source of contamination to the subsequent sample.

The major problem associated with metering small quantities of liquid is the inability to successfully deliver such quantities in a reproducible manner. During the process of liquid sample dispensing, the volume of a liquid drop, which may be on the order of 50 microliters, is 10 to 100 times the volume of sample required for some analyses. Consequently the process of liquid dispensing must be precisely controlled to insure adequate dispensing precision, i.e., the ability to dispense exactly the same volume of a sample each time.

Various approaches have been taken to improve liquid dispensing. One such approach, described by Reichler et al., in U.S. Pat. No. 4,121,466, is the placement of an immiscible fluid upon the outer surface of the aspirating probe of a dispensing system. Reichler uses a coaxial liquid dispenser to flow an immiscible liquid e.g., silicone oil, over the surface of the aspirating probe. Such liquid selectively wets the interior and exterior surfaces of the probe and the interior surfaces of the conduit system, to prevent the deposit of aqueous sample residues upon such surfaces. The immiscible fluid is dispensed, along with an air segment, between aspirations of successive samples, each dispensed air and sample segment being encapsulated by such immiscible fluid while passing through such system. The disadvantage of this system is the contamination of the sample mixture with the "immiscible" fluid and the inability of the system to precisely control the liquid drop formation and dispensed volume.

U.S. Pat. No. 4,259,291, issued to Smythe, describes a system which improves upon the Reichler et al. system by directly applying the immiscible fluid to the surface of the probe in a uniform and precisely controlled manner. This provides for the delivery of small volume aliquots of aqueous fluid, but once again suffers from the contamination problem.

A different approach to sample delivery is disclosed in a patent issued to Chen, U.S. Pat. No. 3,869,068. Here Chen utilizes an inner needle coaxially disposed in an outer conduit. The sample is dispensed through the inner needle and then a diluent is dispensed through both the inner needle and outer conduit. This accomplishes rapid and convenient liquid dispensing but cannot insure precise, reproducible sample delivery or dilutions since the sample aspiration is not controlled as to wetting of the outer surface of the inner needle.

Toshiba use a syringe pipette on their TBA580 Clinical Analyzer. The syringe tip is a metal needle. With this system the needle is washed after obtaining the sample liquid. Each aliquot is washed into the respective reaction/analysis chamber. The wash is water which is squirted at the sample needle by a separate flush needle (non-contacting, non-coaxial). This system suffers from the large amount of flush water required and the imprecision due to the water that remains on the sample and flush needles after dispensing.

SUMMARY OF THE INVENTION

Many of the precision dispensing problems of the prior art are solved by the method and system of this invention. According to the method, small samples of a first liquid are aspirated and dispensed using a probe having inner and outer coaxially disposed conduits defining a coaxial region by: aspirating the first liquid into the inner conduit and the annular space between the conduits, flushing the annular space with a second liquid miscible with the first liquid to remove the first liquid from the annular space and hence the exterior of the inner conduit and establish a controlled interface between the conduits, dispensing a predetermined quantity of the first liquid from the inner conduit into the second liquid in the coaxial region, and flushing the annular space with a predetermined quantity of the second liquid thereby dispensing the first liquid.

The method may include contacting the tip of the outer probe with a surface to remove excess liquid prior to dispensing and flushing. Also, the inner conduit can alone be extended axially for immersion in the first liquid prior to aspiration, and withdrawn into the outer conduit prior to the initial flushing.

This method has many advantages. For one, it provides for better volumetric repeatability since the sample is directly dispensed into a miscible carrier fluid. This eliminates the uncertainty associated with surface tension effects and drop adhesion to the needle tip. Also, since the outside surface of the inner needle is flushed with an inocuous second liquid prior to sample aspiration, sample-to-sample contamination is reduced.

An apparatus that may be used to effect the method set forth above comprises: an outer conduit having inlet and supply ends, a diluent pump means connected to the supply end of the outer conduit for supplying a diluent liquid thereto, an inner conduit having inlet and supply ends and coaxially disposed in the outer conduit defining an annular space therebetween, a sample pump means connected to the supply end of the inner conduit, means for immersing the inlet end of the inner conduit in a first liquid miscible in the diluent liquid, and means for selectively actuating the sample pump means to aspirate the first liquid into the inlet end of the inner conduit, means for dispensing a portion of the aspirated first liquid by selectively actuating the first and second pumps to flush the annular space at the inlet end of the outer conduit with the diluent liquid and to dispense a portion of the first liquid from the inner conduit into the diluent liquid.

Other configurations may take the form of an outer conduit of reduced diameter at the inlet end, an inner conduit of reduced diameter at the inlet end, or reduced diameter at the inlet ends of both the inner and outer conduits.

In a preferred form of the invention, the inner conduit is positionable along the axis of the outer conduit and is slideably centered relative to that axis by protuberances in the inner wall of the outer conduit.

The coaxial positionable inner movable conduit affords the many advantages set forth above. Samples are accurately and reproduceable dispensed without cross contaminating the reaction mixture. There is also less sample waste due to the smaller surface area wetted by the sample. Also, the external surface of the outer conduit is never in contact with the sample, thereby reducing contamination.

BRIEF DESCRIPTION OF THE DRAWINGS

A better understanding of the invention may be had from the following description taken in connection with the accompanying drawings which:

FIG. 1 is a block diagram of a coaxial pipetting, sampling system constructed in accordance with this invention;

FIG. 2 is a side elevation view of a probe housing assembly constructed in accordance with this invention;

FIG. 3 is a plan view of the probe housing assembly;

FIG. 7 is a cross-sectional side elevation view of a coaxial probe where the outer conduit is of reduced diameter at the inlet end;

FIG. 8 is a cross-sectional side elevation view of a coaxial conduit assembly where the inner conduit is of reduced diameter at the inlet end;

FIG. 9 is a cross-sectional side elevation view of a coaxial probe assembly where both conduits are of reduced diameter at their inlet ends;

FIGS. 11A-C are fragmentary, cross-sectional side elevation views of a fixed inner coaxial probe assembly performing the steps of sample aspiration, initialization, and dispense.

DETAILED DESCRIPTION OF THE PREFERRED EMBODIMENT

Figure 4:
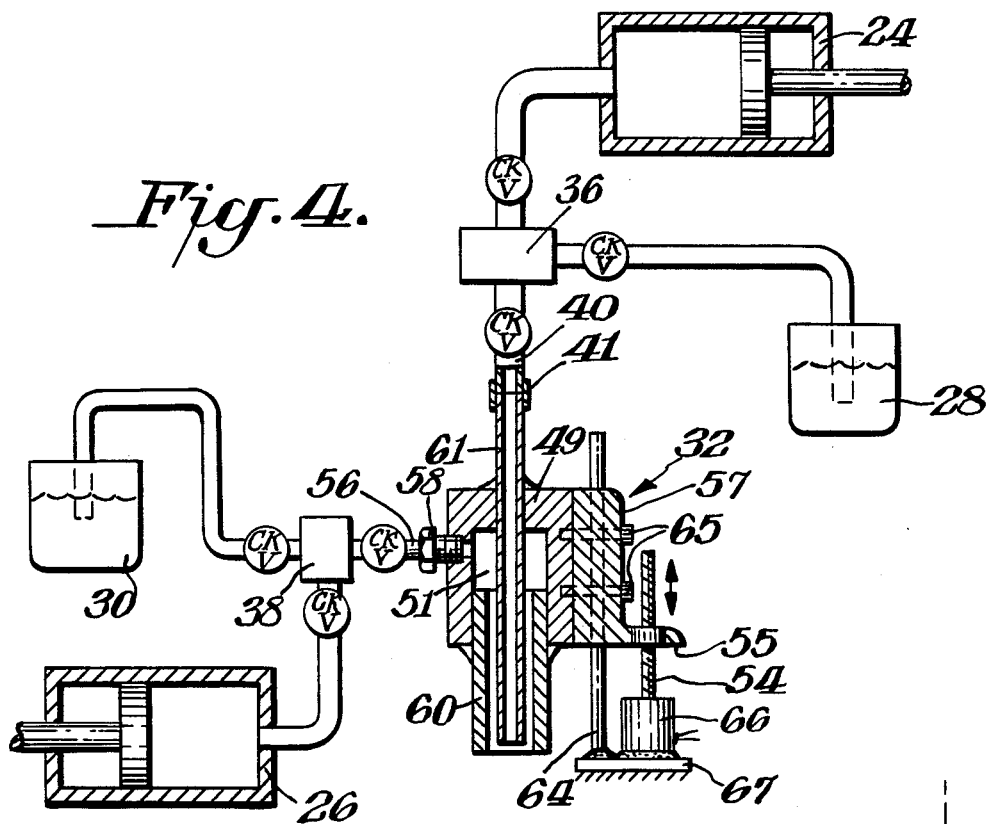
FIG. 4 is a part schematic, part cross-sectional side elevation view of portions of the coaxial pipetting sampling system of FIG. 1 incorporating a fixed inner conduit constructed in accordance with this invention.

There may be seen in FIG. 1 a block diagram of a coaxial pipetting sampling system constructed in accordance with this invention. The apparatus includes a command generator 20, which is used to create the commands which are transmitted to a sample turntable 34 and to a probe sequence controller 22. The probe sequence controller 22 in turn controls the operation of both a sample pump 24 and a diluent pump 26 and the probe assembly 32. The probe sequence controller 22 also regulates the position of selector valves 36 and 38 which connect the diluent pump 26 to either a probe assembly 32 or a first reservoir 30 and the sample pump 24 to either the probe assembly 32 or a second reservoir 28. The probe assembly operates to aspirate samples from a sample turntable 34 as will be described.

Referring to FIGS. 2, 3, and 4 there is seen a coaxial probe assembly 32 constructed in accordance with this invention. The probe assembly 32 has a probe housing 49 (FIG. 4) which defines a manifold 51. An outer conduit 60 is secured to the manifold as by welding and an inner conduit 61 is fixed positioned by the housing 49 and extends downwardly through the manifold 51 and is coaxially and fixedly located within the outer conduit 60 extending to a point just short of the open end of the outer conduit 60.

The housing 49 is mounted to be vertically positionable by way of a helical lead screw 54 driven by stepper motor 66. The stepper motor in turn is controlled by the sequence controller 22. A housing guide rod 64 is vertically mounted to a base 67 to facilitate the vertical displacement of the probe housing 49. The inner conduit 61 is connected through a sample tubing 40 to the selector valve 36 which links the sample pump 24 either to the liquid reservoir 28 or directly to the inner conduit 61. The manifold 51 and hence the outer conduit 60 is connected via a coupling 58 which is secured to the probe housing 49 to a selector valve 38 through tubing 56. The diluent pump 26 is connected through tubing 56 and the selector valve 38 to either the manifold 51 or to the liquid reservoir 30.

The probe assembly is a two-piece construction comprising the probe housing 49 and a support bracket 57, typically fabricated from a non-corrosive metal such as stainless steel and held together via cap screws 65. Housing guide rods 64 communicate with the probe support bracket 57 via a slideable contact means allowing for proper vertical displacement. The lead screw 54 engages a bracket arm 55 as best seen in FIG. 4 to position the probe assembly 32 vertically. The coaxial probe assembly can either be fixed in place as a bench top instrument or can be integrated into a larger apparatus. To facilitate sample access, as in the case of clinical analysis, sample turntable 34 such as the FIA-07, made by Bifok of Sweden can be used in conjunction with the coaxial sampling system for sample analysis.

The sample turntable 34 typically houses a plurality of sample carrying containers 74 which are placed about circumference of a rotatable carousel. The carousel can either be manually rotated into position or programmably controlled. Therefore depending upon application the samples can be positioned such that the probe assembly 32 can easily access the samples for analysis preparation and the like. Illustrated in FIG. 4 is the sample container 74 which is positioned for sample preparation by the sample turntable 34.

The command generator 20 may be a Hewlett-Packard 85 computer and the sequence controller 22 may be an Intel SDK-85 microcomputer. Likewise, the pumps 24 and 26 may be ones manufactured by Hamilton, Inc., of Reno, Nev. having a capacity of 100 and 2500 microliters respectively. The arrangement using the valves 36 and 38 to connect the respective pumps 24 and 26 to either the respective reservoirs 28, 30 or the inner and outer conduits 60 and 61 allows the sample liquid to be flushed from the tips of the conduits 60, 61 without having to draw flush water through the contaminated conduit. Before use, residual oil and dirt is removed from the tips of both conduits by soaking them in a 10 normal sodium hydroxide (50% saturated) solution for 20 minutes followed by rinsing with water.

The inner conduit 61 may be constructed using a 21 ga. thin wall stainless steel needle tubing (part number HTX-21 TW SS 403 from Small Parts, Inc., Miami, Fla. 33138). The tip may be ground flat and approximately normal to the long axis. The outer conduit 60, a 1-inch long, 18 ga. needle (Becton Dickinson, Ruthford, N.J., Courand Needle, catalog #1268), also is ground flat on the tip and calculated to contain 70 microliters of fluid. The probe assembly 32 is then mounted in the probe housing 49 as shown in FIG. 4 with the inner conduit tip recessed within the outer conduit by up to about 1.2 cm. Actually, the inner conduit tip position is limited primarily by the fact that it must remain immersed in the diluent liquid of the outer conduit. Typically, in the recessed addition, this will permit it to extend beyond the tip by the meniscus of the liquid in the outer conduit which is about the inner radius of the outer conduit. Preferably it may be recessed a like amount.

The operation of the probe assembly is most easily understood with reference to FIGS. 11A-11C. These figures illustrate the sequence of events associated with the use of the fixed or non-moveable inner conduit 61. Operating under control of a command generator 22 the sample turntable 34 is actuated to index a new sample container 74 containing a sample 76.

Next, the stepper motor 66 is energized by the sequence controller 22 to lower the probe assembly 32 including the inner and outer conduits 60 and 61 into the sample liquid 76. Both the sample and diluent pumps 24, 26 are energized by the sequence controller 22 to draw sample liquid 76 into the inner conduit 61 and the annular space between the inner and outer conduits 60, 61 as best seen in FIG. 11A. Any liquid already in the needle or conduits 60, 61 is separated from the sample liquid 76 by air bubbles 63 at the liquid innerface. These air bubbles aid in cleaning the conduits.

The probe assembly 32 was lifted and the sample turntable 34 rotated to position a new waste container 74' under the probe assembly. The probe is now lowered into the container 74'. Wash fluid from the annular space is discharged into the container 74' at the same time. Care must be taken in this washing step to minimize the amount of liquid from the wash that adheres to the outer surface of the outer conduit 60. In fact in order to establish a consistent interface between the first and second liquids, an initialization step can be undertaken which consists of dispensing a small amount of sample into the second sample liquid and then flushing with the second liquid through the annular space into the waste container 74'.

The probe assembly is lifted and the sample turntable indexed to the next position with a reaction container 74' under the coaxial conduits. Next a sample aliquot is expressed from the inner conduit 61 into the diluent liquid in the annular space at the tip of the outer conduit. Simultaneously the pump 26 is energized to express the diluent fluid and sample aliquot from the annular space into a reaction chamber 74'. The sample turntable 34 is again indexed to position a wash container (not shown) under the probe assembly and the whole assembly washed in preparation for the next sample, i.e., diluent fluid is passed from both pumps 24, 26 through both the inner conduits 61 and the annular space between the conduits.

To accomplish this, the valves 36 and 38 are switched to connect the respective pumps 24, 26 to the respective diluent or wash reservoirs 28, 30. The pumps 24, 26 are energized to withdraw fluid from the respective reservoirs 28, 30. The valves 36, 38 are then switched to connect the respective pumps 24, 26 to the respective conduits 60, 61.

The advantage of this method and system is the ability of the probe assembly to precisely and repeatedly express relatively small volumes of a sample. This is accomplished as described above by the coaxial probe assembly in which the sample liquid is held in the inner conduit which is surrounded by a coaxially disposed outer conduit containing a liquid miscible with the sample liquid. The sample aliquot is expressed from the inner conduit at the same time the diluent liquid is passed from the annular space surrounding the inner conduit. Thus in effect the sample aliquot is injected into the miscible diluent liquid and flushed by the diluent liquid into the sample receptacle. This provides a high degree of precision and repeatability in being able to dispense precise quantities of sample in a repeated manner.

EXAMPLE I

A coaxial pipetting system with a non-moveable conduit was configured to allow the inner conduit 61 to be approximately 1 millimeter inside the tip of the outer conduit. The inner conduit 61 was filled with 50 microliters water, followed by 1 microliter air. Next 25 microliters of dye was then aspirated by introducing the probe assembly into the dye container until the outer conduit 60 was about 5 millimeters submerged.

The outer surface was then withdrawn and wiped clean with lint-free tissue paper (Kimberly-Clark Kimwipes) and twice the annular space was flushed with 100 microliters of water. One microliter of dye was expelled into the annular space from the inner conduit and 100 microliters of water flushed through the annular space. Using this procedure 10 subsequent aliquots were then delivered and subsequently diluted to 1.5 milliliters yielding absorbance measurements of 1.460, 1.496, 1.476, 1.463, 1.481, 1.455, 1.463, 1,459, and 1.447 using a Hewlett Packard Model HP-8450-A spectrophotometer. The mean was 1.4655 and standard deviation was 0.0146 with a coefficient of variation of 0.999%.

Figure 5:
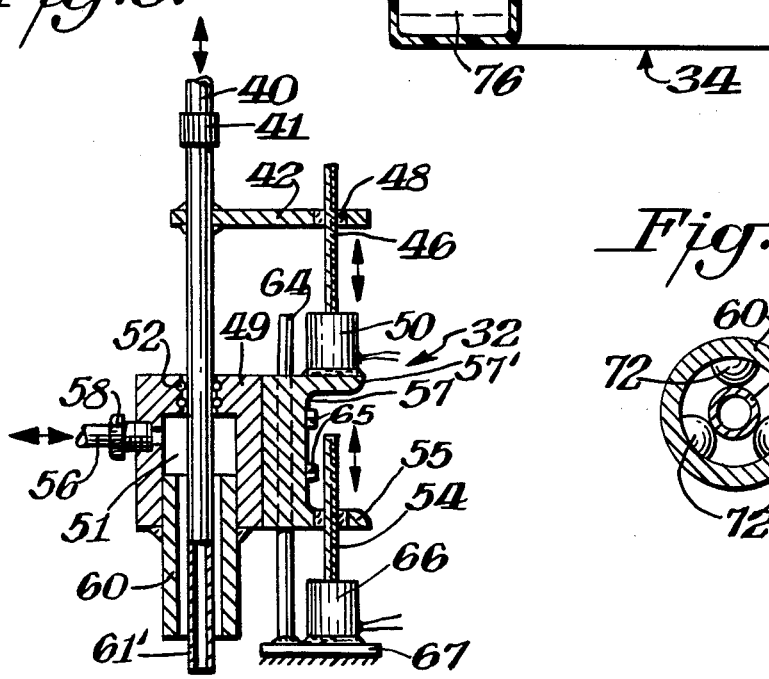
FIG. 5 is a side elevation view of the drive mechanism for a coaxial probe incorporating a moveable inner conduit constructed in accordance with this invention.

FIG. 5 illustrates another embodiment of the instant invention, i.e., a moveable probe sampling system. This system is constructed in similar manner to the fixed probe assembly illustrated in FIG. 4 but with an inner conduit 61' being vertically positionable relative to the outer conduit 60. To facilitate this vertical movement, a stepper motor 50 is positioned on a modified support bracket 57. The motor 50 has a lead screw 46. The lead screw 46 engages a helical bearing 48, which in turn is secured in a support arm 42. The inner conduit 61' is rigidly attached to the support arm 42 by either welding or a clamping means and can therefore be vertically positioned as a function of stepper motor 50 rotation. The stepper motor is controlled by the sequence controller 27. The probe housing 49 is constructed with an axial bore extending into the probe manifold 51. To provide for both a liquid seal and low friction slideable communication of the inner conduit 61 relative to the probe housing 49, circumferential seals 52, typically teflon packing glands are used. The resiliency of the seal 52 facilitates slight transaxials motion, thus providing leak-free operation.

Figure 6:
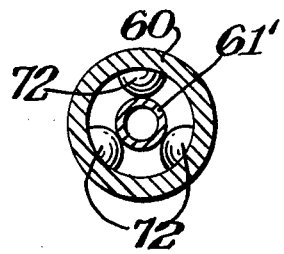
FIG. 6 is a cross-sectional view of a coaxial probe assembly illustrating the support protuberances in the inner wall of the outer conduit.

Illustrated in FIG. 6 is a cross-sectional view of an inner and outer conduit assembly embodying guidance protuberances 54 to maintain the inner conduit 61' in axial alignment with the outer conduit 60. These protuberances can take the form of metallic dimples 54 created by crimping the outer conduit 60 in three radially spaced circumferential positions to a radius slightly larger than the outer diameter of the inner conduit 61'.

The operation of this probe assembly having a moveable inner conduit may be better understood by reference to FIGS. 10A–E. As will be seen, this operation is very much the same as that described for the fixed inner conduit. For this reason, the workings of the sample turntable 34 in conjunction with the raising and lowering of the conduits 60 and 61' all under the control of the generator 20 and controller 22 will be omitted.

Figures 10A, 10B, 10C:
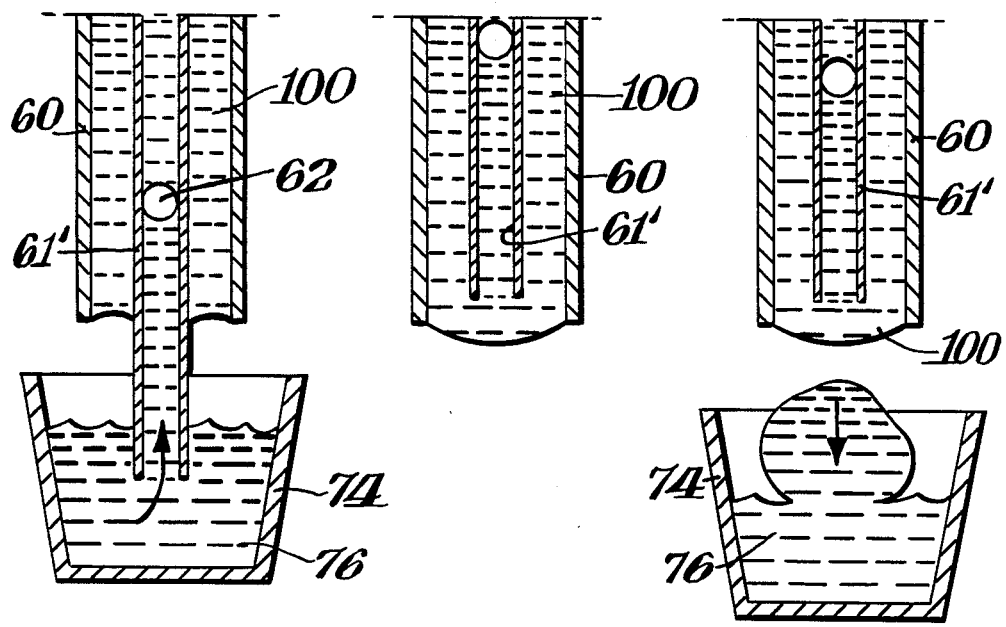
FIGS. 10A-E are fragmentary, cross-sectional side elevation views of a moveable inner coaxial probe assembly, having a moveable inner conduit, performing the steps of sample aspiration, initialization and dispense.

Referring to FIG. 10A, there is seen a coaxial pipetting system with the moveable inner conduit 61 in a protruding position and the probe assembly lowered so that the inner conduit drops into a sample container 76. In this position a sample aliquot can be drawn into the inner conduit 61' alone. This sample aliquot is typically separated from the diluent or wash liquid by an air bubble interface 62 as previously described. Subsequently, the inner conduit 61' is retracted to a position as illustrated in FIG. 10B in which the inner conduit 61' is within the outer conduit 62 so that the tip of inner conduit 61' is surrounded by diluent or wash liquid. In this position the sample liquid adheres to the outer surface of the inner conduit 61'. This is washed away by a diluent or wash liquid 100 which is passed through the annular space between the inner conduit 61' and outer conduit 60 as illustrated in FIG. 10C. Upon completion of the washing, the inner conduit 61' tip remains completely surrounded by wash liquid 100 as illustrated in FIG. 10D.

Figures 10D, 10E:
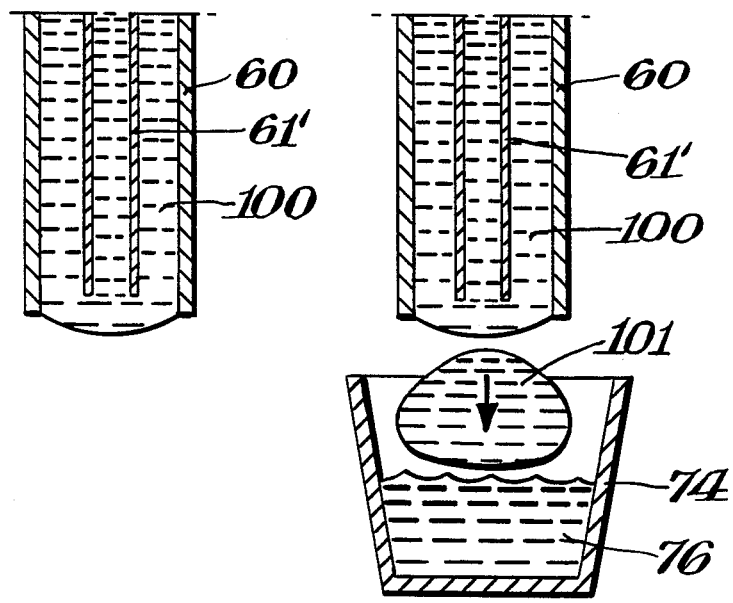

Next, a desired quantity of sample liquid 76 is expressed from the inner conduit 61', which is still in the withdrawn position, as shown in FIG. 10E, directly into the diluent liquid in the annular space. The resulting droplet mixture 101, FIG. 10E, is washed into a reaction chamber 74 by the action of liquid 100 passing through the annular space between the inner and outer conduits 60–61'. By these operations, contaminating liquids have been removed from the conduit surfaces and the surface tension effects on the sample liquid 76 is minimized so that the precision of the sample aliquot is improved. In fact in order to establish a consistent interface between the first and second liquids, an initialization step can be undertaken which consists of dispensing a small amount of sample into the second sample liquid and then flushing with the second liquid through the annular space into the waste container 76.

A coaxial pipetting system, with a moveable inner conduit was constructed using an inner conduit 61 made from a 24 inch long section of 21 ga. thin wall stainless steel needle tubing (part number HTX-21 TW SS 403 from Small Parts, Inc., Miami, Fla. 33138). The tip was swaged to reduce the inner diameter from 0.023 inch to 0.010 inch and ground flat and approximately normal to the long axis. The outer conduit 60, a 1 inch long, 18 ga. needle (Becton Dickinson, Rutherford, N. J., Cournand Needle, catalog #1268), which was also ground flat on the tip but not swaged. The coaxial needle assembly was then mounted in the probe housing 49 as shown in FIG. 5. The inner conduit was calculated to contain 70 microliters of fluid. The long length of inner needle tubing was used to avoid junctions which have dead volumes which contribute to carry-over of one sample to the next, causing cross-contaminations. The use of a larger bore tubing would help reduce the length. However, it is desirable to minimize the size of the orifice at the tip, since the reproducibility of the sample liquid boundary is on the order of a hemisphere with a diameter equal to the diameter of the orifice. The swaging operation achieves a compromise. Furthermore, long tubing with a narrow bore will have a very large and undesirable pressure drop even at moderate liquid flow rates.

EXAMPLE II

In an actual test that was run, the sample pump 24 was filled to 50% capacity with water. The valve 38 was switched to the inner conduit and the pump withdrew 1 microliter air, 1 microliter dye, 1 microliter air, and 25 microliter dye. The dye in a small container was manually lifted up to the protruding inner conduit 62 until the conduit was about 5 millimeters submerged. Second, the inner conduit was withdrawn and 1 microliter expelled from the inner conduit 61 into the annular space and 100 microliters of water flushed through the annular space. The amount of water hanging from the outer conduit 60 was controlled by touching the needle to the side of the receiving container. Third, 10 subsequent aliquots were delivered to 1.5 millimeter capacity acrylic cuvettes by expressing 1 microliter from the inner conduit 61 into the annular space followed by 100 microliters water being pumped through the annular space. Finally, the sample pump 24 was emptied and the annular space flushed with water. Several sample cuvettes were made ready for spectrophotometric analysis by adding 1 milliliter of water to each. The cuvette contents were mixed 5 times by inversion and their absorbance read at 520 nanometers on a Hewlett Packard Model HP-8450-A. spectrophotometer. The following data were obtained: 1.539, 1.565, 1.564, 1.543, 1.558, 1.560, 1.564, 1.515, 1.550, 1.532. The average was 1.553 with a standard deviation of 0.012 or a coefficient of variation of 1.1% showing good precision.

An alternative embodiment to the coaxial sampling probe assembly can be seen in FIGS. 7, 8, and 9. These embodiments incorporate a variety of advantages depending upon the desired end use. FIG. 7 illustrates a coaxial conduit assembly where the outer conduit 82 is of reduced diameter at the inlet tip. This reduced cross-sectional area provides for a higher velocity fluid flow at the inlet tip, creating a better washing of the outer surface of the inner needle and, in addition, it reduces the uncertainty of the volume dispensed of the second liquid because of a reduced miniscus. This configuration affords a further advantage of providing for a reduced pressure drop due to the larger outer conduit diameter 84, while maintaining a small cross section 82 at the inlet tip.

FIG. 8 illustrates a coaxial conduit assembly where the inner conduit 86 is of reduced diameter at the inlet tip. This design contains more first liquid per unit surface of the inner conduit while maintaining a small miniscus and hence small uncertainty of the interface between the first liquid and second liquid.

FIG. 9 illustrates a coaxial conduit assembly where both conduits are of reduced diameter at their inlet ends. This configuration combines the advantages of both FIG. 7 and FIG. 8 as defined in the above writing.

When the term "diluent" liquid is used in this specification and claims, it is understood to include water or saline or buffer solutions, or other suitable diluting or wash liquid. In some cases, it may be a reagent solution although this can cause undesired or premature reactions to occur.

The method and system of this invention have many advantages. For one, the system provides for better volumetric repeatability since the sample is directly dispensed into a miscible carrier fluid (diluent or wash liquid), thus eliminating the uncertainty associated with surface tension effects and drop adhesion to the needle tip. Also, since the outside surface of the inner conduit is flushed with second liquid prior to sample aspiration, sample-to-sample contamination is minimized. Also, the inner conduit is free to slideably move relative to the inner conduit providing for easy sample access. There is less sample waste due to the smaller surface area wetted by the sample. In the case of the movable inner conduit, the external surface of the outer conduit is never in contact with the sample, thereby reducing contamination. A variety of inner and outer conduit diameter combinations provide for reduced cross-sectional area at the tip of the orifice, thereby minimizing the interfacial surface of the liquid therein contained while at the same time minimizing peripheral surface area contact with the inner conduit.

I claim:

1. A liquid pipetting system for aspirating and precisely dispensing small samples of a first liquid, having an outer conduit having outlet and supply ends; means connected to the supply end of the outer conduit for supplying a liquid thereto; an inner conduit having inlet and supply ends and coaxially disposed in the outer conduit to define an annular space therebetween; a sample pump means connected to the supply end of the inner conduit; means for immersing the inlet end of the inner conduit in the first liquid; and means for selectively actuating the sample pump means to aspirate the first liquid into the inlet end of the inner conduit; the system characterized by a diluent pump connected to the supply end of the outer conduit for supplying a diluent liquid miscible with the first liquid thereto, and means for dispensing a portion of the aspirated first liquid by selectively activating the pumps to dispense a portion of the first liquid from the inner conduit into the diluent liquid in the annular space and simultaneously to flush the inlet end of the inner conduit with the diluent liquid.

2. A system as set forth in claim 1 wherein the outer conduit has an axis and the inner conduit is positionable along the axis.

3. A system as set forth in claim 2 wherein the inner conduit is slideably supported by protuberances in the inner wall of the outer conduit.

4. A system as set forth in claim 2 wherein the immersing means incudes means for selectively extending only the inner conduit into the first liquid for aspiration.

5. A system as set forth in claim 1 wherein the immersing means includes means for dipping the inlet ends of the conduits in the first liquid, and means to selectively activate the diluent pump to aspirate the first liquid to the annular space.

6. A system as set forth in claim 1 wherein the outer conduit is of reduced diameter at the inlet end.

7. A system as set forth in claim 1 wherein the inner conduit is of reduced diameter at the inlet end.

8. A system as set forth in claim 1 wherein both conduits are of reduced diameter at their inlet ends.

9. A method for accurately aspirating and dispensing small samples of a first liquid using a probe having inner and outer coaxially disposed conduits defining a coaxial region comprising the steps of:
 aspirating the first liquid into the inner conduit;
 flushing the annular space between the conduits with a second liquid miscible with the first liquid to remove the first liquid from the entire exterior of the inner conduit and establish a controlled interface between the first and second liquids;
 dispensing a predetermined quantity of the first liquid from the inner conduit into the second liquid in the annular space; and
 flushing the annular space with a predetermined quantity of the second liquid thereby precisely dispensing the first liquid.

10. A method set forth in claim 9 which includes the additional step of contacting the tip of the outer probe with a surface to remove excess liquid prior to dispensing and flushing; and
 initially aspirating the first liquid into the annular space as well as the inner conduit.

11. A method as set forth in claim 9 wherein the inner conduit alone is extended axially for immersion in the first liquid prior to aspiration, and
 withdrawn into the outer conduit prior to the initial flushing.

12. A method as set forth in claim 11 which includes the additional step of contacting the tip of the probe with a surface to remove excess liquid prior to dispensing and flushing.

* * * * *